United States Patent [19]

Flanagan et al.

[11] 4,156,813
[45] May 29, 1979

[54] DETECTOR MODULE FOR GAS MONITOR

[75] Inventors: Brian S. Flanagan, San Diego; Phillip L. Turner, Del Mar; Richard D. Broce, Vista; Peter L. Lagus, Olivenhain, all of Calif.

[73] Assignee: Systems, Science and Software, La Jolla, Calif.

[21] Appl. No.: 818,764

[22] Filed: Jul. 25, 1977

[51] Int. Cl.² ............................................. G01T 1/18
[52] U.S. Cl. ..................................... 250/381; 250/379
[58] Field of Search .............. 250/374, 375, 379, 381, 250/382, 384, 393

[56] References Cited

U.S. PATENT DOCUMENTS

| | | | |
|---|---|---|---|
| 2,551,531 | 5/1951 | Freedman | 250/379 |
| 3,104,320 | 9/1963 | Speakman et al. | 250/381 |
| 3,277,296 | 10/1966 | Dimick et al. | 250/381 |
| 3,828,184 | 8/1974 | Lupton | 250/381 |

Primary Examiner—Davis L. Willis
Attorney, Agent, or Firm—Fitch, Even & Tabin

[57] ABSTRACT

A detector module for use in a gas monitor assembly to measure changes in electron flow resulting from absorption of electrons in an electron capture gas includes an internal housing for containing a radioactive source and electrodes suitably spaced apart to permit gas flow therepast. The internal housing along with couplings for interconnection with a gas flow source, a gas receiver and suitable electronic receiver means are disposed within a detector housing having integrally attachable closure means, the detector housing and closure means providing shielding for the radioactive source while being adapted in combination to prevent operating access to the couplings in order to prevent accidental or undesired exposure of the internal housing and radioactive source.

12 Claims, 3 Drawing Figures

DETECTOR MODULE FOR GAS MONITOR

BACKGROUND OF THE INVENTION

The present invention relates to a radioactive source director module for use in a gas monitor and more particularly to such a detector module which is adapted to contain the radioactive source and other detector components, to permit sealed coupling of those components with other portions of a gas monitor and to prevent accidental or undesired exposure of the radioactive source.

Generally, the present invention relates to a tracer gas monitor designed to sample and determine the presence of an electron capture tracer gas. A sample or test gas, containing the tracer gas, is conventionally injected into a flow of carrier gas. The carrier gas containing the tracer gas is caused to flow through an electron capture detector containing spaced apart electrodes and a source of ionizing electrons such as a radioactive material.

The tracer gas is selected from a class of gases capable of absorbing electrons which would otherwise be collected upon one of the two electrodes. Thus, the presence of the tracer gas within the carrier gas flowing through the detector tends to reduce electron flow to one of the electrodes which is measured by conventional external electronic means. With electronic circuitry for the gas monitor being calibrated with respect to the carrier gas, the concentration of the tracer gas passing through the detector may be closely determined by suitable reference to a calibration chart.

Within such gas monitors, the carrier gas is conventionally an inert gas such as nitrogen or argon. The tracer gas may be a suitable gas capable of electron capture such as sulphur hexafluoride which is a non-radioactive, non-toxic inert gas. Other examples of suitable tracer gases include fluorocarbons such as those available under the tradename Freon as well as other halogenated compounds.

Gas monitors of the type described above are generally well known in the prior art as may be seen for example with reference to U.S. Pat. No. 3,714,421 issued Jan. 30, 1973.

The present invention is particularly concerned with the use of radioactive materials employed as electron sources in such monitors. Commonly, it is desirable for the gas monitors to be used by personnel who are otherwise untrained in the handling of radioactive materials. In addition, it is sometimes necessary to change the radioactive source within a gas monitor depending upon the particular application for which the monitor is being used.

Accordingly, there has been found a need for an improvement in such gas monitors permitting their use by such personnel while assuring against accidental or undesired removal of the radioactive material from the monitor or undesired or accidental exposure of the radioactive material.

SUMMARY OF THE INVENTION

Accordingly, it is an object of the invention to provide a detector module for use in a gas monitor to contain the electrodes and a radioactive electron source as conventionally required therein, the detector module further including an internal housing for containing the electrodes and radioactive electron source with couplings for providing sealed connection of the internal housing with various portions of the monitor, the detector module also including a detector housing and closure means adapted to contain the internal housing and to prevent accidental or undesired disconnection of the couplings.

In this manner, the detector module may have a housing constructed of a suitable material for shielding the radioactive source. Through use of the combination referred to above, the detector module may be removed from or inserted into gas monitor assemblies by personnel otherwise untrained in the handling of radioactive materials while assuring against accidental or undesired exposure to the radioactive material.

Preferably, the detector housing and closure means contain the internal housing and couplings with the closure means preferably being integrally secured to the detector housing so that destruction of one or the other of those components is necessary in order to remove the internal housing with the radioactive source or to disconnect the couplings.

Additional objects and advantages of the invention are made apparent in the following description having reference to the accompanying drawings.

DESCRIPTION OF THE PREFERRED EMBODIMENT

Figure 1:
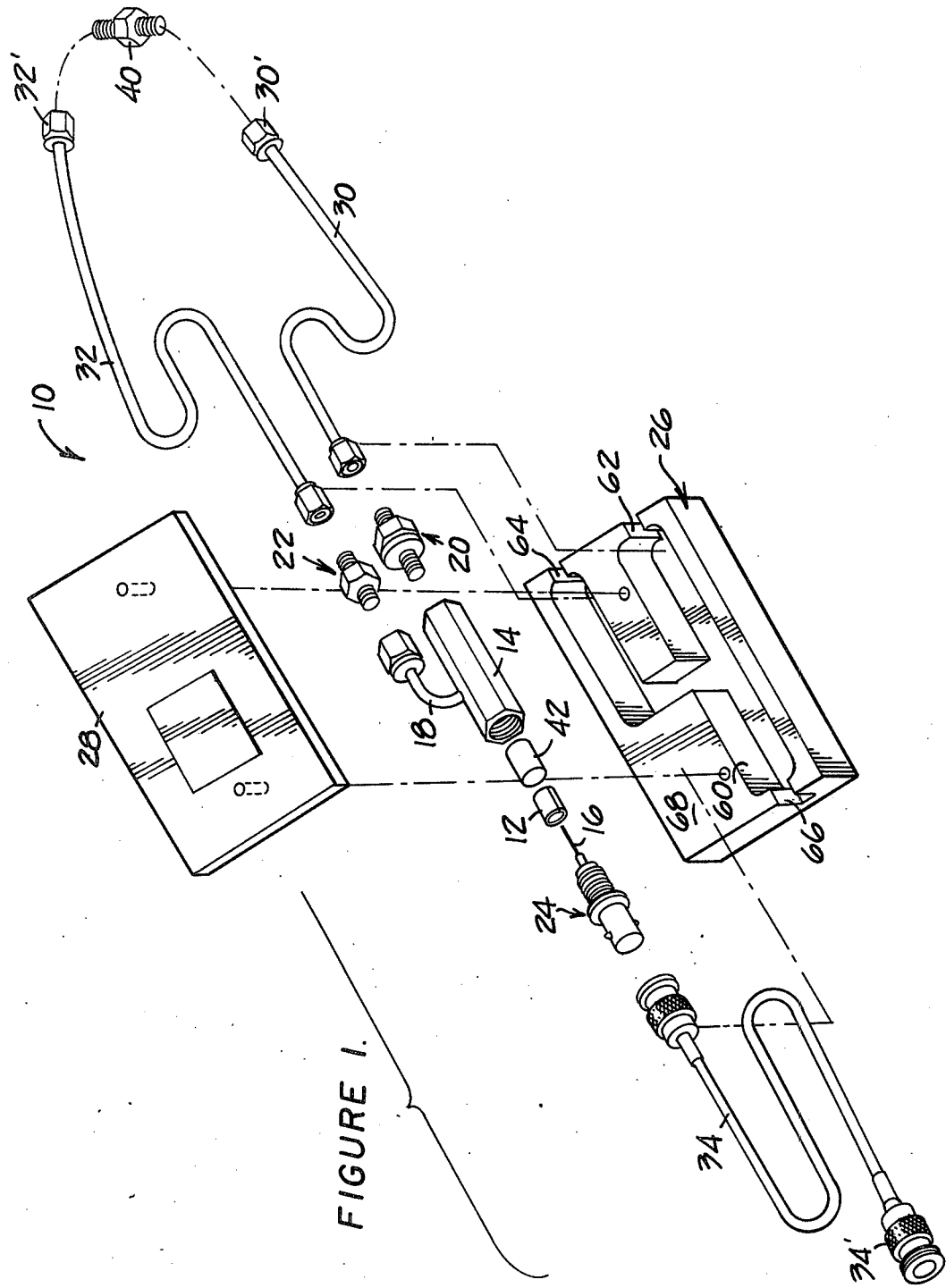
FIG. 1 is an exploded isometric view of the components in a detector module constructed according to the present invention.

Referring particularly to FIG. 1, the detector module of the present invention is contemplated for use in a gas monitor where a tracer gas is caused to flow past two electrodes and an electron source. The tracer gas is selected to partially absorb and thereby reduce electron flow toward one of the electrodes to permit monitoring the amount of tracer gas flowing therepast by suitable electronic means. Accordingly, the detector module is contemplated for use in such a gas monitor which includes a conventional gas flow source and a gas receiver to which gas from the detector module may be returned. In addition, the gas monitor conventionally includes suitable electronic circuitry for receiving an electrical signal from the detector module representative of a tracer gas passing therethrough.

Figure 2:
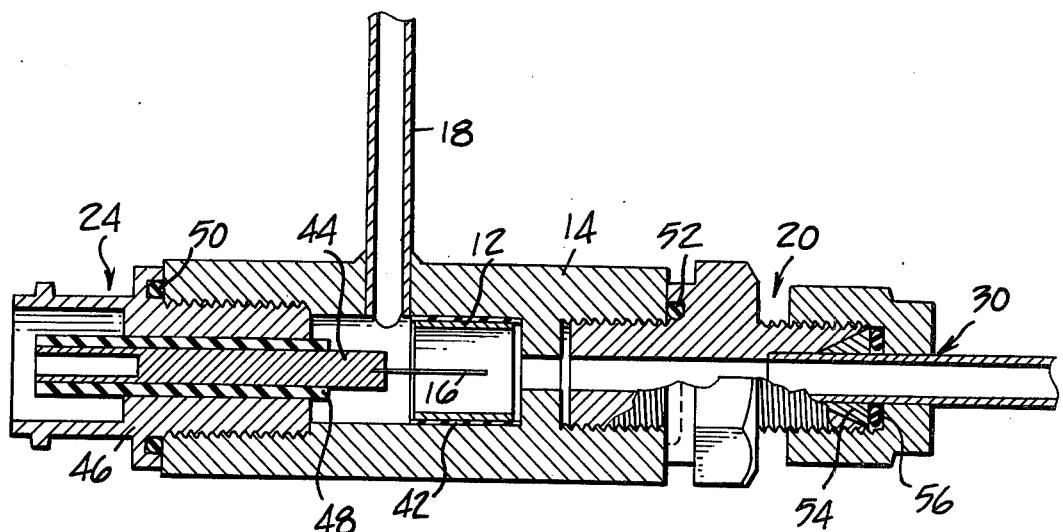
FIG. 2 is an axially sectioned view of an internal housing for the detector module which contains the electrodes and radioactive electron source for accomplishing detection.

Referring now particularly to FIGS. 1 and 2, a detector module of the type contemplated by the present invention is generally indicated at 10. A radioactive electron source 12 is contained within an internal housing 14. The internal surface of the housing 14 forms one electrode while the other electrode is formed by an electron-capture wand 16 which extends concentrically through the cylindrical radioactive source 12.

Gas flowing through the internal housing 14 is received by a sidearm 18 for return to the gas monitor in a manner described in greater detail below. First and second couplings 20 and 22 are adapted for sealed connection with one end of the internal housing 14 and the sidearm 18 in order to connect the interior of the internal housing 14 with the gas source and gas receiver of the monitor. Preferably, the first coupling 20 is connected with the gas source and is suitable for introducing gas into the interior of the housing 14 to flow axially between the concentrically spaced apart radioactive source 12 and the electron-capture wand 16. The gas then passes through the sidearm 18 for return through the coupling 22.

A third coupling 24 is preferably connected with the other end of the internal housing 14 and serves two additional functions. Initially, the third coupling 24 acts as a coaxial connector for the two electrodes formed by the wand 16 and the housing 14 itself with suitable electronic circuitry in the gas monitor. In addition, the third coupling 24, like the first and second couplings 20 and 22, serves to seal the interior gas flow passages of the internal housing 14 and its sidearm 18.

The internal housing 14 and the sidearm 18, along with the first, second and third couplings 20, 22 and 24, are adapted to be received by a detector housing 26 and confined therein by a closure or cover indicated at 28. Both the housing 26 and closure 28 preferably provide radioactive shielding for the source 12. In addition, they are adapted for integral attachment to each other in order to prevent operating access to the couplings 20, 22 and 24. This prevents accidental or undesired disconnection which would effectively expose the radioactive material 12. The specific construction of the housing 26 and cover 28 is described in greater detail below.

The first, second and third couplings 20, 22 and 24 each preferably include an external conduit respectively indicated at 30, 32 and 34. The external conduits extend outwardly from the detector housing 26 and each include additional coupling means respectively indicated at 30', 32' and 34' for connection with the gas supply, the gas receiver and electronic circuitry in the gas monitor. In order to facilitate removal of the detector module for replacement in a gas monitor or for transfer to a different gas monitor, the additional coupling means 30' and 32' for the first and second couplings 20 and 22 are adapted to be sealed by a common external fitting generally indicated at 40.

To describe these components of the detector module in greater detail, the radioactive source 12 is preferably formed as a split foil which is shaped as a cylinder and disposed within the internal housing 14. The radioactive source 12 is preferably a 300 millicurie titanium-tritide foil which is insulated from the housing 14 by means of an insulating cylinder generally indicated at 42 in FIG. 2. The insulation 42 may be formed from suitable plastic insulation, available under the Mylar trade name for example, having a typical thickness of 1 mil. The radioactive source 12 is thus supported by the inside surface of the housing 14 while being insulated therefrom by means of the insulator 42.

The wand 16 is supported by a central axial connector 44 in the third coupling 24. An outer portion 46 of the third coupling is insulated from the connector 44 by means of an annular insulator 48 while being adapted for electrical contact with the housing 14. With the third coupling 24 being threaded into engagement with the housing 14, the separate conductors 44 and 46 are respectively connected with the two electrodes of the detector. Thus, the external conduit 34 may be a conventional coaxial connector suitable for connection with the third coupling. In addition, the third coupling 24 includes an O-ring or similar means indicated at 50 to assure a seal between the third coupling 24 and the housing 14.

The internal housing 14 itself is preferably constructed from stainless steel. Through the arrangement referred to above, gas is delivered from the first conduit for axial flow between the radioactive source and the wand 16. As may be seen in FIG. 2, the wand extends substantially through the length of the radioactive source. It may also be best seen from FIG. 2 that gas passing through the cylindrical radioactive source 12 then enters the sidearm 18 for return to the gas receiver of the monitor through the second coupling 22, the external conduit 32 and the additional coupling means 32'.

Referring particularly to FIG. 2, it may also be seen that the first coupling 20 is fitted into one end of the housing 14 and includes sealing means such as an O-ring 52 to maintain a seal between those components. Additional sealing means are provided to ensure a seal between the coupling 20 and the external conduit 30. Those sealing means include a swaged seal element 54 and an O-ring 56. Referring also to FIG. 1, the second coupling 22 is of substantially similar construction as described above for the first coupling 20. Thus, the second coupling 22 also includes seal means (not otherwise shown) acting against the sidearm 18 and the external conduit 32 after assembly.

The housing 26 and closure 28 are preferably formed from relatively thick shielding material such as a suitable plastic to assist in containment of the radioactive source 12. Preferably, the housing 26 and cover 28 are constructed from a plastic such as that available under the tradename LUCITE.

Referring particularly to FIG. 1, the housing 26 is formed with an h-shaped cavity 60 for receiving the internal housing 14 and the sidearm 18 as well as the first, second and third couplings 20, 22 and 24. Each leg of the h-shaped cavity 60 includes a slot indicated respectively at 62, 64 and 66. The slots 62–66 are only large enough to receive the external conduits 30, 32 and 34. Thus, they serve to allow the internal housing 14 and assembled couplings in other components to be installed within the housing 26. However, the slots prevent operating access to the couplings 20–24 and thus prevent them from being accidentally or unintentionally uncoupled to effectively expose the radioactive source 12.

The cavity 60 is sized so that the housing 14 and sidearm 18 are nested in place with the couplings 20, 22 and 24 abutting the respective end portions of the cavity which form the slots 62, 64 and 66. In this manner, the housing 26 has greater thickness to provide increased shielding for the radioactive source 12. At the same time, the abutting engagement of the couplings 20, 22 and 24 with end portions of the cavity prevents them from working loose and maintains them in sealed engagement with the internal housing 14.

Figure 3:
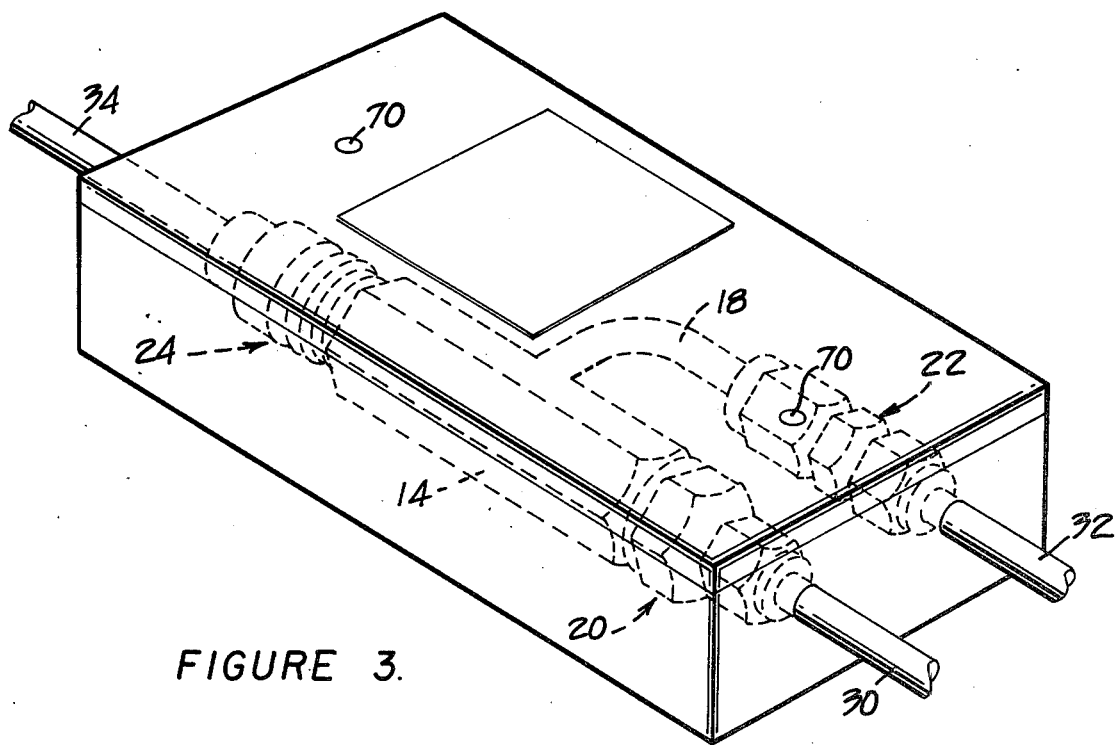
FIG. 3 is an isometric view of the internal housing and associated couplings contained within a detector housing and confined therein by an integrally attached closure.

With the internal housing 14 and couplings 20, 22 and 24 being arranged within the housing 26, the cover 28 is then arranged upon the housing to close the h-shaped cavity 60. The cover is then integrally attached to the housing for example by means of cement applied for example to the exposed surface 68 of the housing as seen in FIG. 1. Suitable mounting holes indicated at 70 in FIG. 3, are provided for securing the detector module within the gas monitor. FIG. 3 illustrates the internal housing 14 and the first, second and third couplings arranged and confined by the integrally attached housing 26 and cover 28 with the external conduits 30, 32 and 34 extending for connection in the manner described above.

With the cover 28 being integrally secured to the housing 26 for example by means of cement, it is essentially necessary to destroy either or both the housing 26 and cover 28 in order to gain access to the internal housing or couplings 20, 22 and 24. Thus, the detector module of the present invention is believed to provide substantial safety during its conventional use within gas monitors of the type referred to above.

Various modifications are believed possible within the scope of the present invention in addition to those made apparent in the preceding description. Accordingly, the scope of the present invention is defined only by the following appended claims.

What is claimed is:

1. In a radioactive source detector adapted for use in a gas monitor assembly to detect changes in electron flow between two electrodes caused by partial absorption of the electrons in an electron capture gas flowing between the electrodes, the monitor assembly including a gas flow source, a gas receiver and an electronic assembly for receiving a signal from the detector, the improvement comprising
an internal source housing for containing the radioactive source and electrodes while forming suitable passages for gas flow therepast,
first, second and third couplings adapted for sealed connection with said internal housing and respectively with the gas flow source, the gas receiver and the electronic means of the monitor assembly,
a detector housing shaped to receive said internal source housing and said first, second and third couplings, and
closure means integrally attachable to said detector housing to enclose said internal source housing and said first, second and third couplings, said detector housing and closure means being adapted in combination to prevent operating access to said couplings after said source housing and couplings are arranged within said detector housing and said closure means is integrally attached thereto.

2. The radioactive source detector module of claim 1 wherein the radioactive source is cylindrical and concentrically spaced apart from an electron capture wand interconnected with one of the electrodes, the first coupling being arranged to axially introduce gas from the gas flow source between the cylindrical radioactive source and the wand.

3. The radioactive source detector module of claim 2 wherein said internal source housing includes a sidearm connected with said second coupling for receiving gas flow after its passage between the cylindrical radioactive source and the wand.

4. The radioactive source detector module of claim 3 wherein said internal source housing is formed as a cylinder with said first and third couplings being threaded into sealed engagement with opposite ends thereof.

5. The radioactive source detector module of claim 4 wherein each of said first, second and third couplings includes conduit means extending externally of said detector housing with additional coupling means for respective sealed connection with the gas flow source, the gas receiver and the electronic means.

6. The radioactive source detector module of claim 5 further comprising means for sealed interconnection with the additional coupling means of the first and second couplings in order to enclose the radioactive source when the detector is uncoupled from the gas flow source and gas receiver.

7. The radioactive source detector module of claim 5 wherein said detector housing is internally shaped to receive said internal source housing and its sidearm as well as said first, second and third couplings, said detector housing comprising first, second and third slots through which said respective external conduits for said first, second and third couplings may extend outwardly from said detector housing, said closure means being a cover integrally attachable to said detector housing, said first, second and third slots being large enough to receive said external conduits while preventing operating access to said first, second and third couplings respectively.

8. The radioactive source detector module of claim 7 wherein said detector housing internally forms a cavity shaped to receive said internal source housing and sidearm in closely fitting relation, wall portions of said cavity adjacent said first, second and third slots being disposed for abutting engagement with said first, second and third couplings to maintain them in sealed connection with said internal housing.

9. The radioactive source detector module of claim 8 wherein said detector housing and said closure means are formed from material adapted to confine radiation from the radioactive source.

10. The radioactive source detector module of claim 1 wherein said detector housing and said closure means are formed from relatively thick material adapted to confine radiation from the radioactive source.

11. The radioactive source detector module of claim 10 wherein said closure means is integrally attachable to said detector housing so that destruction of either or both the detector housing and closure means is required in order to obtain access to said internal source housing and said first, second and third couplings.

12. The radioactive source detector module of claim 1 wherein said closure means is integrally attachable to said detector housing by means requiring destruction of either or both the detector housing and closure means in order to obtain access to said internal source housing and said first, second and third couplings.

* * * * *